United States Patent
Pitts et al.

(10) Patent No.: US 10,076,392 B2
(45) Date of Patent: Sep. 18, 2018

(54) APPARATUS AND METHOD FOR MINERALISING BIOLOGICAL MATERIAL

(71) Applicant: King's College London, London (GB)

(72) Inventors: Nigel Pitts, Ninewells (GB); Christopher Longbottom, Ninewells (GB); Joseph Crayston, St. Andrews (GB)

(73) Assignee: Reminova LTD, Perth (GB)

( * ) Notice: Subject to any disclaimer, the term of this patent is extended or adjusted under 35 U.S.C. 154(b) by 562 days.

(21) Appl. No.: 14/593,283

(22) Filed: Jan. 9, 2015

(65) Prior Publication Data
US 2015/0125808 A1    May 7, 2015

Related U.S. Application Data

(63) Continuation of application No. PCT/GB2013/000296, filed on Jul. 9, 2013.

(30) Foreign Application Priority Data

Jul. 10, 2012    (GB) .................................. 1212222.2

(51) Int. Cl.
*A61C 19/06*    (2006.01)
*A61M 37/00*    (2006.01)
(Continued)

(52) U.S. Cl.
CPC ............ *A61C 19/06* (2013.01); *A61C 1/0015* (2013.01); *A61K 33/42* (2013.01);
(Continued)

(58) Field of Classification Search
CPC ....... A61C 19/06; A61C 1/0015; A61C 33/92; A61K 47/48246; A61K 33/42;
(Continued)

(56) References Cited

U.S. PATENT DOCUMENTS 3,019,787 A * 2/1962 Simmons ............... A61C 19/06
604/20
4,149,533 A * 4/1979 Ishikawa ............... A61C 19/06
604/20
(Continued)

FOREIGN PATENT DOCUMENTS

CN    1527693 A    9/2004
CN    1972642 A    5/2007
(Continued)

OTHER PUBLICATIONS

Office Action in corresponding Chinese Application No. 201380046224X, dated Aug. 29, 2016.
(Continued)

*Primary Examiner* — Nicholas Lucchesi
(74) *Attorney, Agent, or Firm* — Edell, Shapiro & Finnan, LLC

(57) ABSTRACT

An apparatus for mineralizing a biological material includes an ultrasonic source, operable to generate an ultrasonic signal, an ultrasonic probe and one or more mineralizing probes, operable to receive a mineralizing agent. The mineralizing agent is transferred from at least one mineralizing probe to the biological material using the ultrasonic signal. Also disclosed are a mineralization agent and a method of mineralizing a biological material that includes the steps of: providing an ultrasound source, providing a mineralizing agent, generating an ultrasonic signal from the ultrasound source, and applying the ultrasonic signal and the mineralizing agent to the biological material separately, sequentially or simultaneously.

22 Claims, 7 Drawing Sheets

(51) Int. Cl.
*A61N 1/30* (2006.01)
*A61N 1/32* (2006.01)
*A61C 1/00* (2006.01)
*A61K 33/42* (2006.01)
*A61K 47/48* (2006.01)
*C01B 25/32* (2006.01)
*C01B 25/455* (2006.01)
*C07K 14/47* (2006.01)
*A61K 9/00* (2006.01)

(52) U.S. Cl.
CPC ... *A61K 47/48246* (2013.01); *A61M 37/0092* (2013.01); *A61N 1/30* (2013.01); *A61N 1/306* (2013.01); *A61N 1/325* (2013.01); *C01B 25/32* (2013.01); *C01B 25/455* (2013.01); *C07K 14/4732* (2013.01); *A61K 9/0009* (2013.01)

(58) Field of Classification Search
CPC ..... A61M 37/0092; A61N 1/30; A61N 1/306; A61N 1/325; C01B 25/32; C01B 25/455; C07K 14/4732
USPC .......................................................... 433/86
See application file for complete search history.

(56) References Cited

U.S. PATENT DOCUMENTS

| | | | |
|---|---|---|---|
| 4,162,576 A | 7/1979 | Takemoto et al. | |
| 6,230,050 B1* | 5/2001 | Pitts | A61B 5/053 600/547 |
| 6,997,883 B1* | 2/2006 | Hahn | A61C 19/04 600/300 |
| 8,961,179 B2* | 2/2015 | Longbottom | A61C 19/063 433/215 |
| 2003/0194382 A1 | 10/2003 | Chang et al. | |
| 2003/0208235 A1* | 11/2003 | Miller | A61N 1/30 607/3 |
| 2006/0008767 A1 | 1/2006 | Whalen | |
| 2006/0194164 A1 | 8/2006 | Altshuler et al. | |
| 2007/0157404 A1 | 7/2007 | Brewer et al. | |
| 2009/0022672 A1 | 1/2009 | Reynolds | |
| 2010/0104519 A1 | 4/2010 | Chung et al. | |
| 2010/0135921 A1 | 6/2010 | Hughes et al. | |
| 2010/0150974 A1 | 6/2010 | Butler et al. | |
| 2010/0303925 A1* | 12/2010 | Pitts | A61K 6/033 424/602 |
| 2011/0264028 A1 | 10/2011 | Ramdas et al. | |
| 2012/0085647 A1* | 4/2012 | Longbottom | A61C 19/063 204/474 |
| 2012/0252046 A1* | 10/2012 | Fei | A61B 5/145 435/14 |
| 2015/0018752 A1 | 1/2015 | Unger et al. | |

FOREIGN PATENT DOCUMENTS

| | | |
|---|---|---|
| CN | 101115527 A | 1/2008 |
| CN | 101212924 A | 7/2008 |
| CN | 101378720 A | 3/2009 |
| CN | 101500640 A | 8/2009 |
| CN | 101600442 A | 12/2009 |
| CN | 101663018 A | 3/2010 |
| CN | 102223917 A | 10/2011 |
| JP | 2010155786 A | 7/2010 |
| JP | 2011518215 A | 6/2011 |
| JP | 2012500078 A | 1/2012 |
| WO | 9742909 A1 | 11/1997 |
| WO | 2006017097 A1 | 2/2006 |
| WO | 2007143796 A1 | 12/2007 |

OTHER PUBLICATIONS

International Search Report and Written Opinion in counterpart International Application No. PCT/GB2013/000296, dated Jan. 31, 2014 (also submitted on Jan. 9, 2015).

Office Action in corresponding Chinese Application No. 201380046224X, dated Dec. 17, 2015.

Office Action in corresponding Japanese Application 2015521055, dated Jun. 5, 2017, along with English Translation.

* cited by examiner

APPARATUS AND METHOD FOR MINERALISING BIOLOGICAL MATERIAL

CROSS-REFERENCE TO RELATED APPLICATIONS

This is a Continuation of International Application PCT/GB2013/000296, with an international filing date of Jul. 9, 2013, and the complete disclosure of which is incorporated into the present Continuation by reference. The following disclosure is also based on and claims the benefit of and priority under 35 U.S.C. § 119(a) to British Patent Application No. GB 1212222.2, filed on Jul. 10, 2012, which is also incorporated in its entirety into the present Continuation by reference.

FIELD OF AND BACKGROUND OF THE INVENTION

The present invention relates to an apparatus and method for mineralising biological material and in particular for re-mineralising demineralised and hypo-mineralised tissue, such as tooth or bone.

Caries is the decay of tooth or bone. Dental caries (also known as dental decay, caries or carious lesions) is caused by acids produced by microbial enzymatic action on ingested carbohydrate. The acids decalcify (demineralise) the inorganic portion of the tooth initially creating a sub-surface lesion, the organic portion then disintegrates leading to the creation of a cavity. In dentistry, demineralisation of a tooth through the development of a carious lesion can be described in terms of the depth of the carious lesion.

Dental caries is commonly treated by the removal of the decayed material in the tooth and the filling of the resultant hole (cavity) with a dental amalgam or other restorative material. In more severe cases, the entire tooth may be removed. Prior to lesion cavitation, it is possible to heal or reverse the tissue destruction by remineralising the caries lesions. However, this process works better where exogenous (e.g. salivary- or food-derived) proteins and lipids have been removed from the caries lesions.

It is known that the level of tooth decay alters the electrical characteristics of a tooth. This arises because as minerals are lost the porosity of the tooth increases and the consequent increased numbers of ions within the pores increase the conductivity i.e. the electrical transport in the tooth. Consequently, demineralisation of a tooth will result in an enhancement of its charge transport properties. This may be manifested in a decrease in the potential difference which must be applied to a demineralised tooth, compared with a healthy tooth, in order to achieve a comparable current therethrough. Correspondingly, this may be manifested in an increased current measurable from a demineralised tooth, compared with a healthy tooth, on application of the same potential difference. These effects can be detected on application of a constant current or constant potential difference respectively.

Alternatively, the impedance (which includes the DC resistance) can be monitored by using AC signals.

There are a number of devices specifically designed to detect dental caries by the application of an alternating electrical current to a tooth using a probe or contact electrode and counter electrode. As described above, the main source of impedance in the circuit formed by the counter electrode and the probe is provided by the tooth and therefore changes to the impedance of the circuit give a measure of changes in the impedance of the tooth. This technique is described in international patent application WO97/42909.

Iontophoresis is a non-invasive method of propelling a charged substance, normally a medication or a bioactive agent, using an electric current. It is known to use iontophoresis in transdermal drug delivery. Iontophoresis may also be used in conjunction with fluoride containing compounds to treat dentine hypersensitivity and to remineralise non-cavitated dental caries lesions. Iontophoresis devices typically include an active electrode assembly and a counter electrode assembly each coupled to opposite poles or terminals of a voltage source. The active agent can be cationic or anionic and the voltage source can be configured to apply the appropriate voltage polarity based upon the polarity of the active agent. The active agent may be stored in for example, a reservoir such as a cavity or in a porous structure or a gel.

Ultrasound is a longitudinal pulse. It is known to use ultrasound for trans-dermal drug delivery—sonophoresis. In dentistry ultrasound is known generally for cleaning, e.g. removal of calculus from the external surface of teeth or debris from the pulp chamber and root canal inside a tooth during root canal treatment.

Electrosonophoresis is a combination of iontophoresis and ultrasound.

SUMMARY

It is an object of the present invention to provide an improved apparatus, system and method for mineralising biological material.

In accordance with a first aspect of the invention there is provided apparatus for mineralising a biological material, the apparatus comprising an ultrasonic source, operable to generate an ultrasonic signal, an ultrasonic probe and one or more mineralising probes, operable to receive a mineralising agent, wherein the mineralising agent is transferred from at least one mineralising probe to the biological material using the ultrasonic signal.

At least one mineralising probe may be the ultrasonic probe.

According to one embodiment, the apparatus comprises an iontophoresis probe.

The apparatus of the present invention may utilise electrosonophoresis.

The apparatus advantageously further comprises a first electrode and a second electrode and an electrical signal generator, operable to generate an electrical signal between the first and second electrodes, a detector, operable to detect the electrical response of the electrical signal between the first and second electrodes, and a controller operable to receive the detected electrical response and to control the ultrasonic signal relative thereto.

The apparatus advantageously further comprises a mineralising probe electrode and a modulator, operable to modulate the electrical signal between the mineralising probe electrode and the second electrode and thereby cause the transfer of mineralising agent to the biological material using the electrical signal.

Advantageously, the mineralising probe electrode is the first electrode.

The controller is preferably operable to control modulation of the electrical signal relative to the detected electrical response. The apparatus advantageously further comprises a reference electrode operable to control at least one of the modulation of the electrical signal and the ultrasonic signal.

The controller advantageously comprises a first software module having a dataset which describes the characteristic electrical response of a sample biological material at various stages of mineralisation, and a second software module which compares the data with the detected electrical response and thereby determine any required modification of at least one of the electrical signal and ultrasonic signal.

The second software module may apply a function which defines the relationship between mineralisation and the electrical response in order to compare the data with the detected electrical response and to thereby determine any required modification of at least one of the electrical signal and ultrasonic signal.

Alternatively, the second software module may apply a look-up table containing information on the electrical response of the biological material and its mineralisation in order to compare the data with the detected electrical response and to determine any required modification of at least one of the electrical signal and ultrasonic signal.

The mineralising probe electrode advantageously transfers the mineralising agent to the biological material by iontophoresis.

According to one embodiment, the mineralising probe electrode advantageously transfers the mineralising agent to the biological material by electrosonophoresis.

When used in accordance with the present invention, ultrasound is generally used in the range of between about 20 Hz to 200 MHz; typically from about 5 MHz to about 200 MHz; preferably from about 10 MHz to about 150 MHz; and more preferably from about 100 MHz to about 150 MHz.

There is an inverse relationship between the ultrasound frequency and the particle size which may be applied to the biological material by the apparatus and method of the present invention. The higher the frequency of the ultrasound, the smaller the particle size which may be applied to the biological material by the apparatus and method of the present invention. Using a higher frequency of ultrasound allows a greater range of particle sizes to be utilised.

The detector is advantageously operable to determine, from the electrical response, the presence of at least one of exogenous proteins and lipids on or in the biological material.

The apparatus may further comprise means for applying a conditioning agent.

The conditioning agent may comprise at least one of an oxidising agent, de-proteinising agent and a de-lipidising agent. Generally the conditioning agent comprises more than one of an oxidising agent, de-proteinising agent and a de-lipidising agent, typically the conditioning agent comprises at least a de-proteinising agent and a de-lipidising agent.

The apparatus is advantageously operable to apply the ultrasonic signal and transfer the mineralising agent separately, sequentially or simultaneously.

The apparatus is advantageously operable to apply the ultrasonic signal and the electrical signal separately, sequentially or simultaneously.

The apparatus is advantageously operable to apply the modulated electrical signal and transfer the mineralising agent separately, sequentially or simultaneously.

According to one embodiment, the apparatus is operable to apply the ultrasonic signal and an iontophoresis signal separately, simultaneously or sequentially and/or in combination. Generally the ultrasonic signal and the iontophoresis signal are applied simultaneously.

The apparatus is advantageously adapted for use with hard tissue biological materials such as tooth and/or bone.

Advantageously, the operation of the apparatus of the present invention can be interrupted in order to re-apply the conditioning agent thereby removing exogenous proteins and/or lipids. In accordance with a second aspect of the present invention there is provided a mineralising agent for use with apparatus, as described above, for mineralising biological material.

The mineralising agent may comprise at least one of a source of calcium ions and a source of phosphate ions and source of hydroxyl ions (such as water), optionally in the presence of a source of fluoride ions. Generally the mineralising agent comprises a source of calcium ions and a source of phosphate ions and a source of hydroxyl ions (such as water). Typically the mineralising agent comprises a source of calcium ions, a source of phosphate ions, water, and a source of fluoride ions.

The mineralising agent may be in a form soluble in water or insoluble in water (in an aqueous dispersion) under the conditions generally used to operate the apparatus/conduct the method of the present invention.

The mineralising agent may comprise casein phosphopeptide-amorphous calcium phosphate (CPP-ACP)

The mineralising agent may comprise calcium, phosphate, hydroxyl/water and fluoride.

The mineralising agent may comprise casein phosphopeptide-amorphous calcium fluoride phosphate (CPP-ACFP).

The mineralising agent preferably comprises one or more mineralisation enhancers. More preferably, the mineralising agent comprises two mineralisation enhancers, wherein one of the enhancers is a source of calcium ions and the other is a source of phosphate ions.

The mineralising agent preferably comprises a calcium:phosphate ratio of between 1:1 and 22:10. More preferably, the mineralising agent comprise a calcium:phosphate ratio of between 3:2 and 22:10. More preferably, the mineralisation agent comprises a calcium:phosphate ratio of approximately 10:6.

Alternatively or additionally, at least one of the mineralisation enhancers may comprise strontium.

The mineralisation agent advantageously comprises nano-particles, having an average particle diameter of less than 500 nm, generally less than 100 nm, typically less than 50 nm, preferably less than 10 nm, more preferably from 1 to 10 nm. According to one embodiment, the mineralisation agent consists of nano-particles.

According to one embodiment, the average particle diameter of the mineralisation agent is 1 to 50 nm.

The use of a mineralisation agent comprising or consisting of nano-particles is believed to allow a greater proportion of the mineralisation agent to be forced into the biological tissue, promoting a more efficient mineralising method, and/or greater retention of the mineralisation agent in the biological tissue.

The nano-particles typically comprise at least one of a source of calcium ions, a source of phosphate ions, a source of hydroxyl ions and a source of fluoride ions. Generally the nano-particles comprise calcium hydroxyapatite.

According to a third aspect of the present invention there is provided a kit comprising apparatus for mineralising a biological material, as described above, and a mineralisation agent as described above. The kit may further comprise a conditioning agent.

According to a fourth aspect of the present invention there is provided a method of mineralising a biological material, comprising the steps of: providing an ultrasound source, providing a mineralising agent, generating an ultrasonic signal from the ultrasound source, applying the ultrasonic signal and the mineralising agent to the biological material separately, sequentially or simultaneously.

The method of the present invention generally involves the use of the apparatus as described herein.

According to one embodiment, the method may involve electrosonophoresis.

Whilst the inventors should not be bound by specific underlying theories, it is believed that the use of electrosonophoresis (the combination of ultrasound and iontophoresis), in a method of mineralising biological material allows a greater proportion of the mineralising agent to be forced into the biological material, rather than remaining on the surface of the biological material. This allows a more effective method of mineralisation. More mineralising agent is forced into the biological material in a shorter time period than equivalent methods using only iontophoresis. The use of electrosonophoresis is also believed to promote greater retention of the mineralising agent in the biological material, meaning that the mineralisation of the biological tissue lasts for longer than methods using only iontophoresis, The method may further comprise the step of conditioning the biological material prior to applying at least one of the ultrasonic signal and mineralising agent thereto. The step of conditioning comprises at least substantially removing at least one of protein and lipids from the biological material (generally substantially removing both of proteins and lipids from the biological material). The step of conditioning preferably comprises the application of at least one of a deproteinisation agent and a delipidisation agent.

The method advantageously further comprises the steps of: providing a first electrode and a second electrode, an electrical signal generator and a controller; generating an electrical signal between the first and second electrodes; detecting the electrical response of the electrical signal, between the first and second electrodes; and controlling the ultrasonic signal relative to the detected electrical response.

The method advantageously further comprises the steps of providing a mineralising probe; providing a modulator; modulating the electrical signal between the mineralising probe and the second electrode and thereby cause the transfer of mineralising agent to the biological material using the electrical signal.

The mineralising probe may be provided by the first electrode.

The method advantageously further comprises the step of controlling the modulation of the electrical signal relative to the detected electrical response.

The method advantageously further comprises the step of providing a reference electrode and controlling at least one of the modulation of the electrical signal and the ultrasonic from information derivable therefrom.

The steps of controlling at least one of the ultrasonic signal and the electrical signal relative to the detected electrical response may comprise the steps of: comparing a dataset of characteristic electrical responses derived from a set of samples of biological material at various stages of mineralisation with the detected electrical response; and determining any required modification to at least one of the ultrasonic signal or electrical signal.

The step of comparing the data set may comprise applying a function which defines the relationship between the mineralisation and the electrical response in order to compare the data with the detected electrical response.

Alternatively, the step of comparing the data set may comprise applying a look-up table containing information relating to the electrical response of the biological material and its mineralisation; and comparing the data with the detected electrical response.

The method may further comprise the step of detecting the presence of at least one of proteins (such as exongenous proteins) and lipids on or in the biological material from the detected electrical response; typically detecting the presence of proteins and lipids.

The mineralising agent is generally as described above.

The mineralising agent may comprise casein phosphopeptide-amorphous calcium phosphate (CPP-ACP)

The mineralising agent may comprise calcium, phosphate, hydroxyl/water and fluoride.

The mineralising agent may comprise casein phosphopeptide-amorphous calcium fluoride phosphate (CPP-ACFP).

The mineralising agent may be substantially insoluble in water under the conditions used in the method of the present invention.

According to one embodiment of the present invention, the mineralising agent remains in or on the bone/dental tissue to which is it applied for at least 3 months, generally at least six months, typically at least one year from application thereto.

The mineralising agent advantageously comprises one or more mineralisation enhancers.

More advantageously, the mineralising agent comprises two mineralisation enhancers, wherein one of the enhancers is a source of calcium ions and the other is a source of phosphate ions.

The mineralising agent may comprise a calcium:phosphate ratio of between 1:1 and 22:10.

Preferably, the mineralising agent comprises a calcium:phosphate ratio of between 3:2 and 22:10.

More preferably, the mineralisation agent comprises a calcium:phosphate ratio of approximately 10:6.

Alternatively or additionally, at least one of the enhancers may comprise strontium.

The mineralisation agent advantageously comprises nano-particles. The nano-particles preferably comprise at least one of calcium, phosphate, hydroxyl and fluoride.

The nano-particles may comprise calcium hydroxyapatite.

The method is advantageously adapted for use in mineralising hard tissue such as tooth and/or bone.

BRIEF DESCRIPTION OF THE DRAWINGS

The invention will now be described by way of example only with reference to the accompanying drawings in which.

DETAILED DESCRIPTION OF THE DRAWINGS

The present invention provides an apparatus and method for mineralising a biological material. The invention is particularly suitable for remineralisation of teeth where decay by demineralisation has occurred or for occluding dental tubules to treat dentine hypersensitivity, or for tooth whitening or in the treatment of dental erosion. It will be appreciated that the apparatus and method described herein is not restricted to the remineralisation of teeth but can be used to mineralise other biological material but is particularly applicable to the mineralisation of hard tissue such as, for example, it may be used in the remineralisation of bones for the treatment of osteoporosis, osteopenia or periodontal disease.

Generally the apparatus and method of the present invention involve electrosonophoresis.

In preferred embodiments of the present invention, spatial imaging data or 3D structural information can be used to generate different characterising parameters, including, tracking changes (and/or relative changes) in grey-scale values (in micro-CT images) in a variety of different parallel vectors in any one of many different planes, to generate an average representation of the mineral density changes in the direction of those vectors. The averaging process is performed preferably over the whole volume of the lesion; and the resulting information therefrom is processed to calculate, amongst other parameters, the depth of the carious lesion in the direction of the pulp. In view of the complex spatial geometries of lesions, the image analysis technique provides substantially more information than that normally available to a dentist. Thus, it may be possible to determine other lesion parameters which may be more useful in characterising the loss of mineral density than the traditionally-used lesion depth parameter.

As described previously, changes in the impedance and/or resistance of a tooth can be detected on the application of an AC signal or a DC constant current or constant potential difference. The application of a pulse or square-wave current or potential difference to a healthy or demineralised tooth also yields dynamic information from the plot of current (or potential) vs time.

Figure 1A:
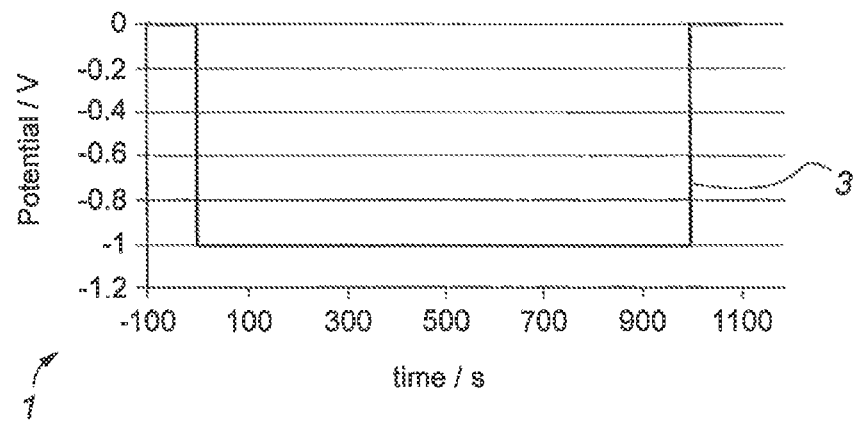
FIGS. 1A and 1B are graphs which show the applied voltage and the current decay rate for a healthy and a demineralised tooth.
Figure 1B:
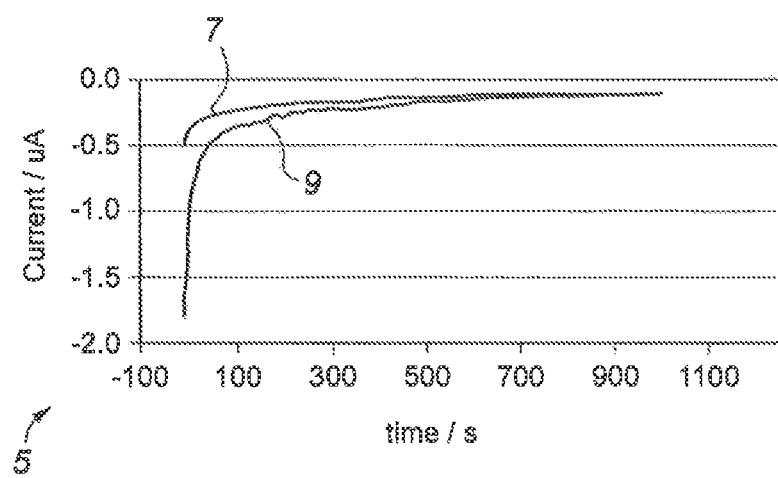

FIG. 1A is a graph 1 of voltage against time which shows a pulsed voltage 3 of substantially constant magnitude. FIG. 1B is a graph of current against time which shows the current decay rate in response to the applied potential difference (voltage) pulse for a healthy tooth and one which has been demineralised. The curve 7 shows the current response for the healthy tooth and the curve 9 shows the response for the demineralised tooth.

Using a mechanistic understanding of charge transport through a tooth and the effect of tooth demineralisation on tooth ionic conductivity, a relation may be formed between the mineral density profiles determined from the above-mentioned image processing technique and a measured temporal electrical response profile. The present invention forms the relation through image-analysis and electrical properties analysis of a large number of healthy teeth and teeth with carious lesions by establishing an analytical model which creates a mathematical function to describe this relationship.

Alternatively, the present invention may employ a look-up table between the measured electrical response data and average mineral density values (determined from the above image analysis techniques) obtained from the studies of the healthy and diseased teeth In establishing the above relation and/or look-up table, micro-CT techniques can be used in which data is calibrated against a plurality of phantoms, so as to ensure that the measured variation in grey scale values is actually representative of a change in mineral density though a tooth, as opposed to an aberrant effect (or imaging artefacts). The above process will be described in more detail below.

The apparatus of the present invention employs a feedback mechanism, wherein an electrical measurement (which may be AC or DC related) is made whilst a tooth is being remineralised by iontophoresis. The electrical measurement is related to the mineral density of a carious lesion in the tooth (through the above-mentioned relation and/or look-up table formed during an offline process) to calculate an appropriate control signal for the apparatus to optimally tune the iontophoretic process.

Figure 2A:
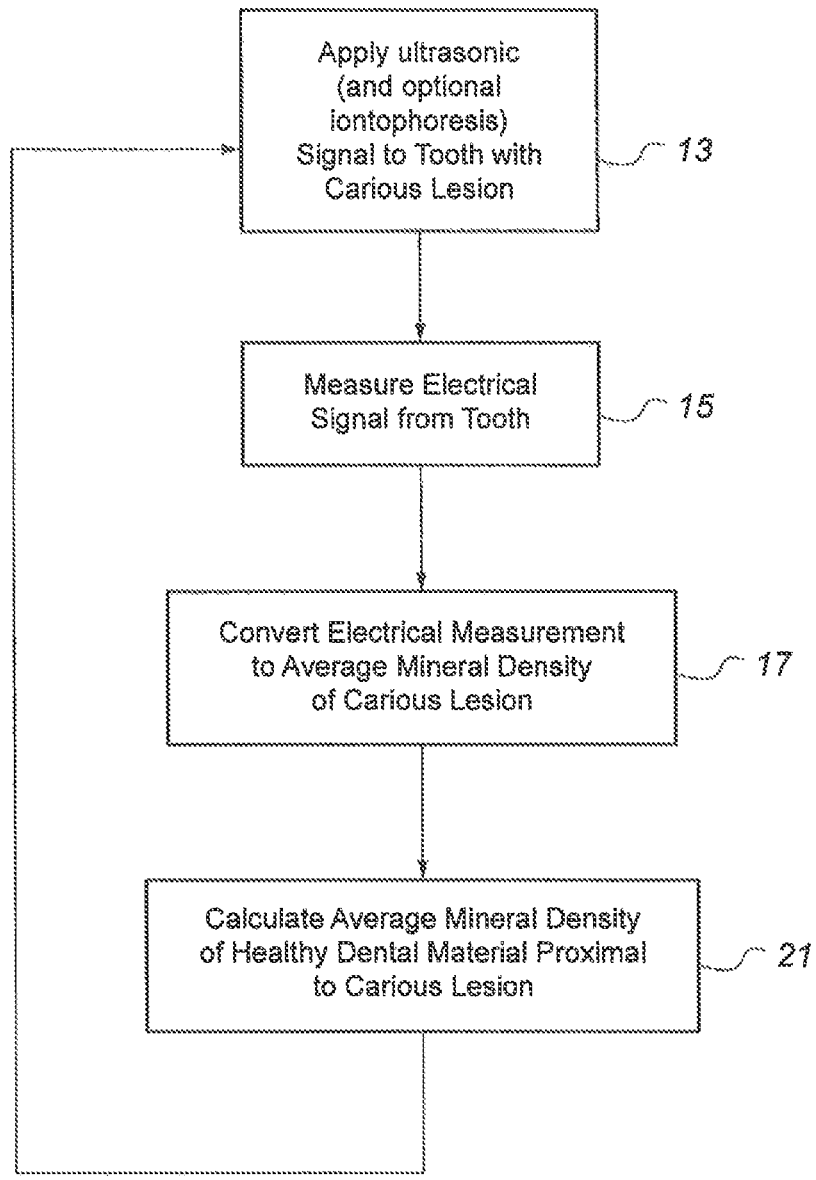
FIG. 2A is a flow diagram which shows an embodiment of the method of the present invention and FIG. 2B is a block diagram of an apparatus for implementing the method of FIG. 2A.

FIG. 2A shows an embodiment of the method of the present invention which comprises the following steps.

Step 0:

A pre-step which involves calibrating the grey-scale values obtained from a micro-CT analysis (used in forming the mineral density values employed in the above-mentioned relation and/or look-up table) a plurality of phantoms (comprising a homogeneous isotropic material which substantially matches dental material) are scanned using a micro-CT device. In the present example, the phantoms comprise hydroxyapatite disks representing a particular material density.

Step I:

Following the micro-CT analysis of the phantoms alone, a plurality of healthy teeth and teeth with carious lesions are each subjected to a similar scanning process, together with the phantoms. The calculated mineral densities of the scanned teeth are processed using a known segmentation technique to identify the boundaries of any lesions therein. A profile of the mineral density is established within the boundaries determined by the segmentation process; and the mineral density profiles are related to a steady-state or temporal electrical measurement obtained from the same teeth.

Step 2:

During the application of an ultrasonic signal and generally, iontophoresis, a constant potential difference or current is applied to a tooth with a carious lesion 13. An electrical response function is measured 15 from the tooth under treatment; and the relation (and/or look-up table) established in Step 1 is used to determine 17 the mineral density of the carious lesion.

Step 3:

The mineral density range of the healthy tooth material proximal to the boundaries established during step 1 is determined 19. This is used to establish the desired degree of remineralisation required of the ultrasonic signal (and generally iontophoretic) treatment.

Step 4:

A change in the magnitude of the ultrasonic (and generally iontophoretic) signal is calculated 21, the calculated change being sufficient to drive mineral into the lesion so that the mineral density of the lesion more closely matches that of the healthy dental material.

Figure 2B:
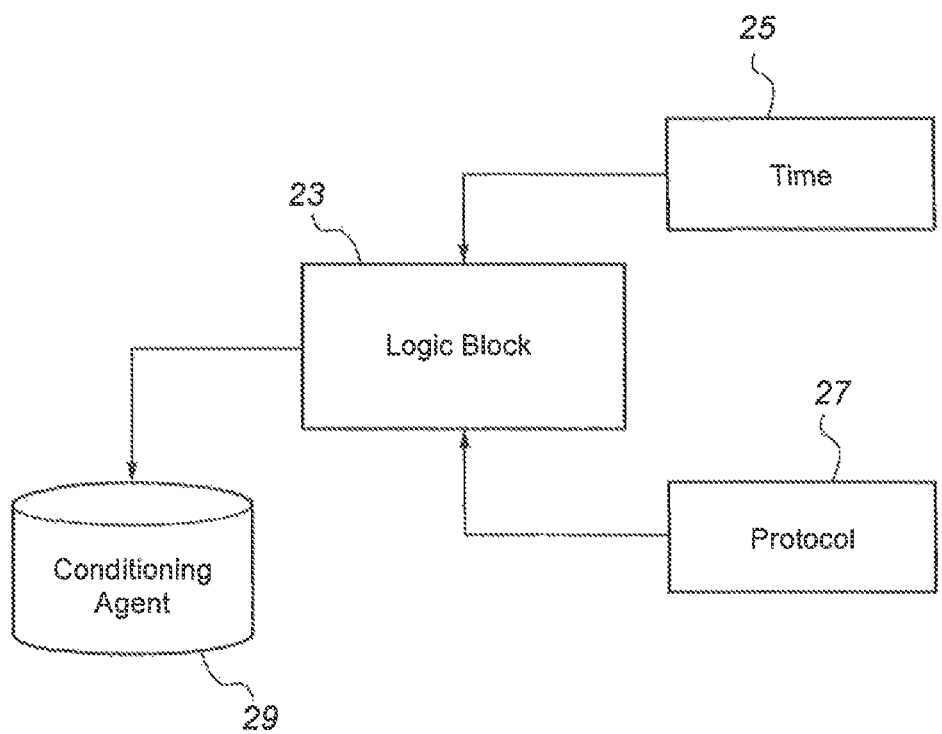

In implementing the method of FIG. 2A, the apparatus of FIG. 2B comprises a logic block 23, which in addition to receiving an indication of the desired change in the magnitude of the ultrasonic (and generally iontophoretic) signal (from Step 4), receives information regarding the time 25 over which the iontophoresis treatment has been operating. The logic block 23 also receives additional protocol information 27 regarding times for example at which the ultrasonic (and generally iontophoresis) should be started or stopped (e.g. to allow the electrical probe to be cleaned and further conditioning agent 29 to be applied thereto).

The apparatus according to the present invention may function to mineralise biological material either using ultrasound alone to propel mineralising agent into the biological material or a combination of ultrasound and iontophoresis.

Figure 3A:
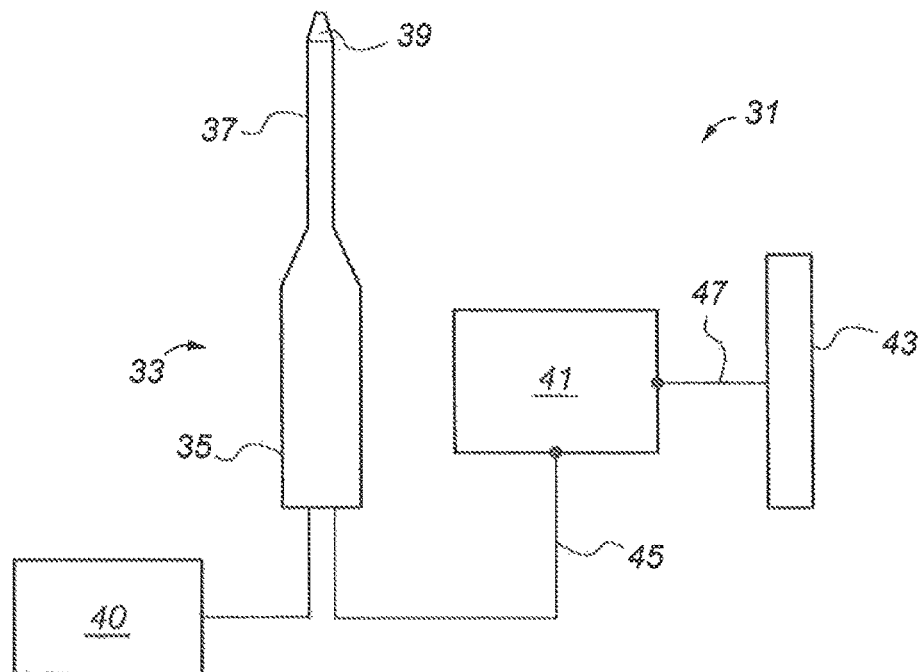
FIGS. 3A and 3B are schematic representations of embodiments of the present invention utilising ultrasound only (FIG. 3A) and combined ultrasound and iontophoresis (FIG. 3B)

FIG. 3A shows a first embodiment of an apparatus 31 for mineralising a biological material, in accordance with the present invention, comprising an ultrasonic probe 33 having a handle 35, a neck 37 and head 39. The ultrasonic probe 33 is connected to an ultrasound source 40 and a controller 41, by cable 45, which in turn is connected to a second counter electrode 43 by cable 47. Electrode 43 may be a hand-held or mouth or lip "loop" electrode.

Figure 3B:
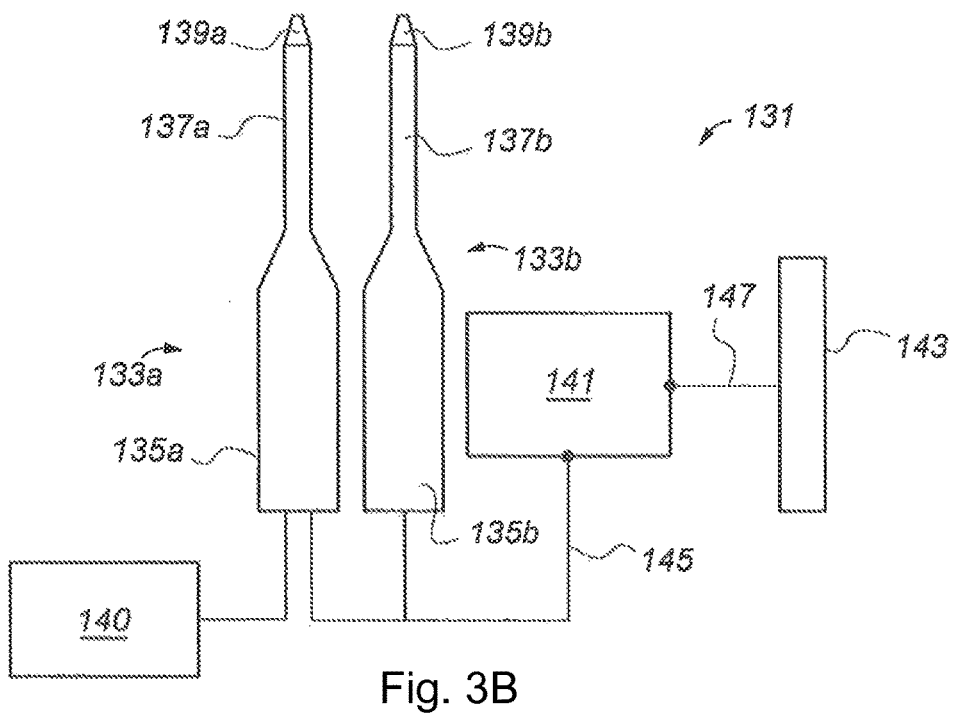

FIG. 3B shows a second embodiment of an apparatus 131 for mineralising a biological material, in accordance with the present invention, comprising an ultrasonic probe 133a having a handle 135a, a neck 137a and head 139a. The apparatus further comprises an iontophoresis probe 133b, operable as a first electrode, having a handle 135b, a neck 137b and a head 139b. The ultrasonic probe 133a is connected to an ultrasound source 140 and a controller 141, by cable 145, which in turn is connected to a second counter electrode 143 by cable 147. Electrode 143 may be a handheld or mouth or lip "loop" electrode. The iontophoresis probe 133b is also electrically connected to the controller 141.

Figure 4:
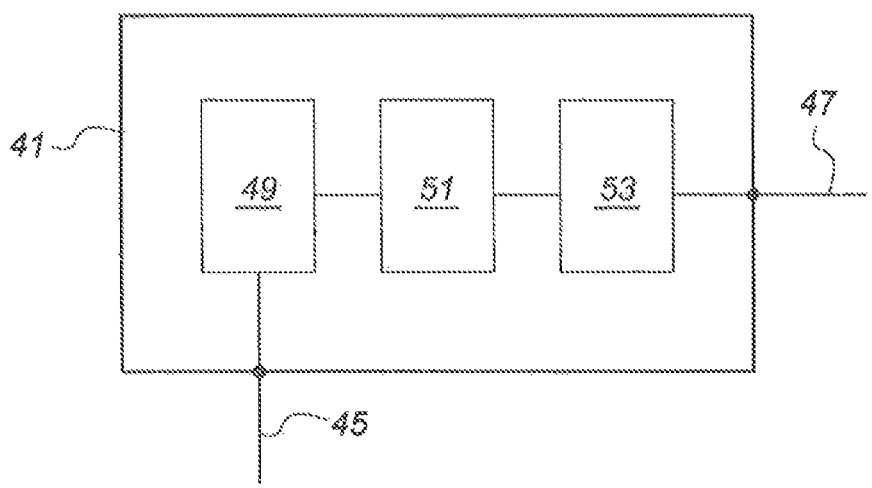
FIG. 4 is a more detailed schematic representation of the controller of the embodiment of FIG. 1.

FIG. 4 shows, in more detail, the controller 41 which comprises a modulator 49 which adjusts the ultrasonic signal to the ultrasonic probe 33a (133a) and, if the iontophoresis probe 133b in accordance with the second embodiment is utilised, modulates the shape and/or frequency and/or amplitude of the waveform sent to the probe 133b.

Figure 5A:
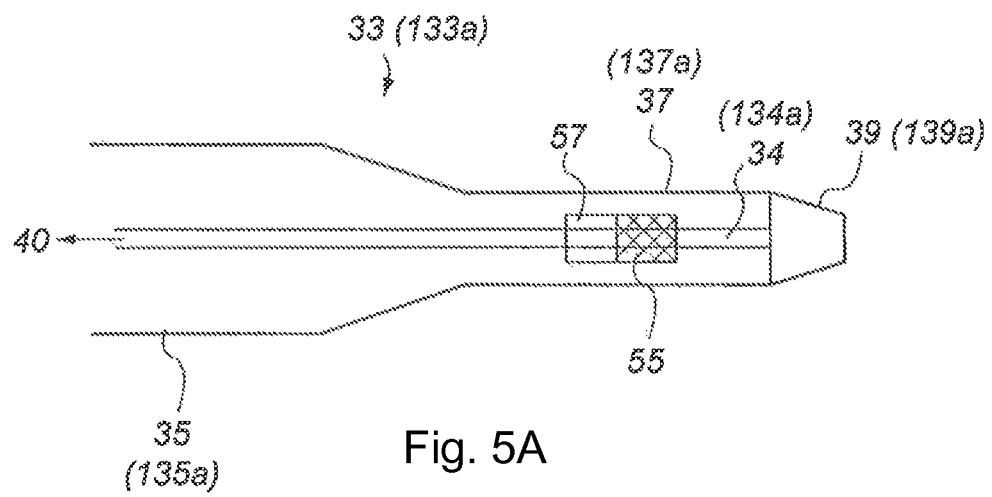
FIGS. 5A and 5B are more detailed schematic representations of the ultrasonic probe and the iontophoresis probe, respectively, of the embodiments of FIGS. 3A and 3B.

FIG. 5A shows the ultrasonic probe 33 (133a), in more detail, wherein it has an ultrasonic waveguide 34 which extends through the handle 34 of the probe to the ultrasound source 40. Disposed between the head 39 (139a) and the ultrasound source 40 is a reservoir 55 (155a) for storing mineralising agent 57 (157a). In use, the mineralisation agent is propelled out from the reservoir 55 (155a) through the head 39 (139a) of the probe 33 (133a) by the ultrasonic signal and into contact with the biological material such as, for example, a tooth or bone.

Figure 5B:
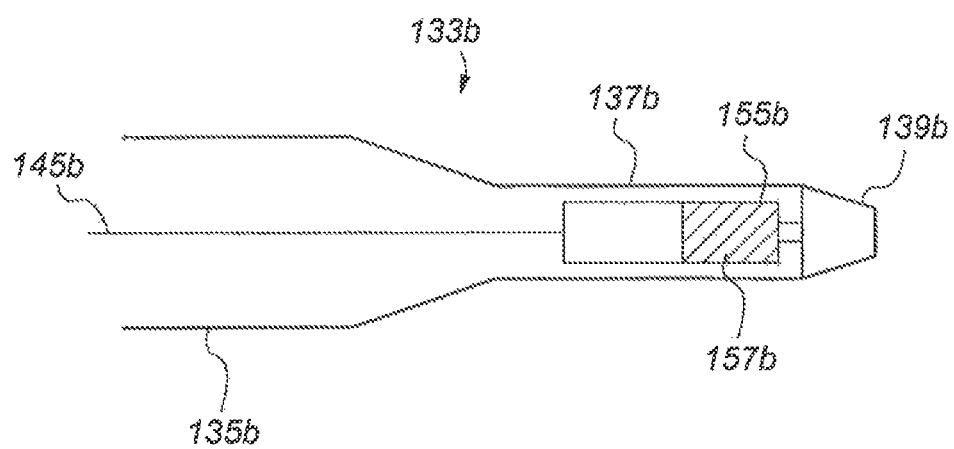

FIG. 5B shows the iontophoresis probe 133b, in more detail, wherein the cable 45 extends through the handle 135b of the probe 133b to a reservoir 155b containing a mineralising agent 157b. In use, the mineralisation agent is propelled out from the reservoir 155b, by the electrical signal (iontophoresis) through the head 139b of the probe 133b and in to contact with the biological material such as, for example, a tooth or bone.

In other embodiments of the present invention, the mineralising agent may be stored in other ways such as in a porous structure or a gel which may be applied directly to a tooth. In embodiments of the present invention where the mineralising agent is stored in a chamber in the probe it can be introduced onto the probe surface by making the chamber of flexible material to allow the mineralising agent to be squeezed out. Alternatively, the chamber may have a plunger or similar component which pushes the mineralising agent out of the chamber.

In order to prevent cross-infection the mineralising agent is typically held separately from the device or embodied as a detachable 'probe tip' which detachably attachable to the end of the probe.

Figure 6:
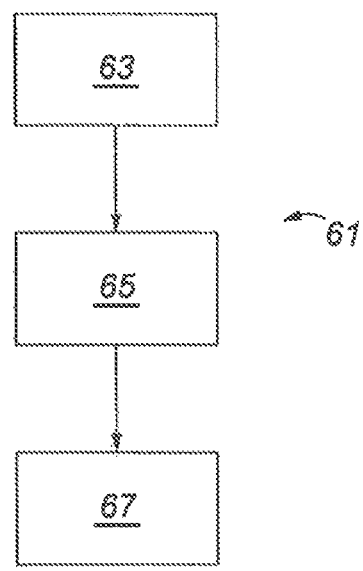
FIG. 6 is a flow diagram showing a first embodiment of the method of the present invention.

FIG. 6 is a flow chart 61 which shows a method of the present invention in which the ultrasonic signal and (if iontophoresis is used) the waveform of the electrical signal in the circuit formed from the first (probe) electrode 33 (133a and/or 133b) and the second counter electrode 43 (143) is controlled so as to transfer a mineralising agent to the biological material 63. The electrical response of the circuit is then detected 65 and the detected signal is analysed so as to determine whether or not the signal needs to be modified and, if so to what extent, in response to the detected electrical response of the circuit 67.

The following example of use of an embodiment of the present invention is given in relation to the remineralisation of teeth. The dentist identifies, within a patient, a specific tooth site which is to be remineralised. Thereafter a conditioning agent is applied and the site is cleansed to remove exogenous proteins and/or lipids from the site. The conditioning agent may be propelled into a hypo-mineralised or demineralised caries lesion, by iontophoresis, utilising the probe and counter electrodes, to optimise the disruption and removal of the exogenous protein and/or lipid content.

The probe 33 (133a/133b) is inserted into the mouth of the patient and on to the tooth site. The counter electrode 43 (143) is connected to the patient. The probe(s), which in this example comprises an ultrasonic (and optionally an iontophoretic) device, propels the mineralising agent 57 (157) through the external surface of the tooth in order to remineralise the caries lesion at that tooth site.

During this process, the electrical circuit formed by the probe(s) 33 (133a/133b), patient and counter electrode 43 (143) provides an output signal which identifies changes in the electrical response of the circuit which have been caused by the ongoing remineralisation process. The electrical response is detected by detector 53, the signal is passed to the controller 51 which processes and compares the electrical response to a dataset of known, experimentally obtained electrical responses to remineralisation. These responses provide 3D structural information on the amount and location of remineralisation of the tooth. The controller is therefore able to send program instructions to the modulator to alter the ultrasonic signal and waveform of the electrical signal input to the probe(s) 33 (133a/133b) by changing its frequency and/or amplitude and/or shape. Once any change to the ultrasonic signal and waveform has been determined, the modulator 49 provides an output to the probe(s) 33 (133a/133b) which in turn determines the manner in which the mineralising agent is propelled through the external surface of the tooth. A response to changes in the remineralisation pattern of the tooth can be made in real time or otherwise.

The comparison of the dataset of known, experimentally obtained electrical responses to remineralisation with the output signal detected by detector 53 requires the creation of a dataset or library of experimentally obtained responses. This information is derived from experimental data in which micro CT images are taken to provide virtual tooth slices. In this example of the present invention, the process is as follows.

A sample having dental caries, or other general defects (e.g. loss of mineral density), is scanned using a 3D tomography system (e.g. x-ray, MRI, neutron (ultrasound). A calibration phantom is used to determine the relationship between attenuation coefficient and electron density; hardware and software solutions are used to minimise intrinsic image artefacts (e.g. beam hardening, ring artefacts, scattering). Reconstruction of the sample is achieved using acquired 2D angular projection images, and is accomplished for different voxel (i.e. 3D pixels) or spatial resolutions. 3D image processing algorithms are employed to calculate spatial distributions of electron density, as represented by attenuation data linked to the phantom. These distributions provide information on the degree of mineralization of relevant volumes of interest.

After ultrasonic (and generally iontophoretic) remineralisation treatment, the sample is rescanned and subjected to the above mentioned methodologies. The subsequent distributions (before and after treatments) of mineral density of relevant volumes of interest are compared to inform of induced changes in mineralization patterns.

This process is repeated for samples with varying degrees of remineralisation to provide information on changes in internal sample structure, which can be related to changes in electrical responses of the sample which occurred during the treatment of the sample. The described technique would inform any spatial heterogeneity of remineralisation, providing feedback from the electrical responses of the sample to the spatial location of remineralisation. Representative experimentally acquired datasets are encoded into the device library to provide characteristic signatures of the spatial location and distribution of mineral densities which enable the clinician to decide on real-time responses to remineralisation patterns. The feedback provided by the integration of the AC impedance or DC resistance values from the sample tooth and its incorporation in the controller, informs the settings of the device in order to optimise the remineralisation of the tissue. Preferably, the initial settings may involve the use of controlled potential coulometry where longer pulses are applied or chrono-amperometry where shorter pulses are applied. Feedback on the nature and extent of the remineralisation process provided by the present invention includes information about if and when to switch the settings to controlled current coulometry to optimise the remineralisation throughout the lesion.

In the case of controlled current coulometry the current is at a constant level which means that the flow of the remineralising agent would be constant also. This would be desirable in promoting a constant rate of remineralisation, since the rate of remineralisation is expected to be directly proportional to the amount of current flowing. Alternatively, the current may be allowed to fall as a function of time and so the rate of remineralisation is not constant with time.

Figure 7:
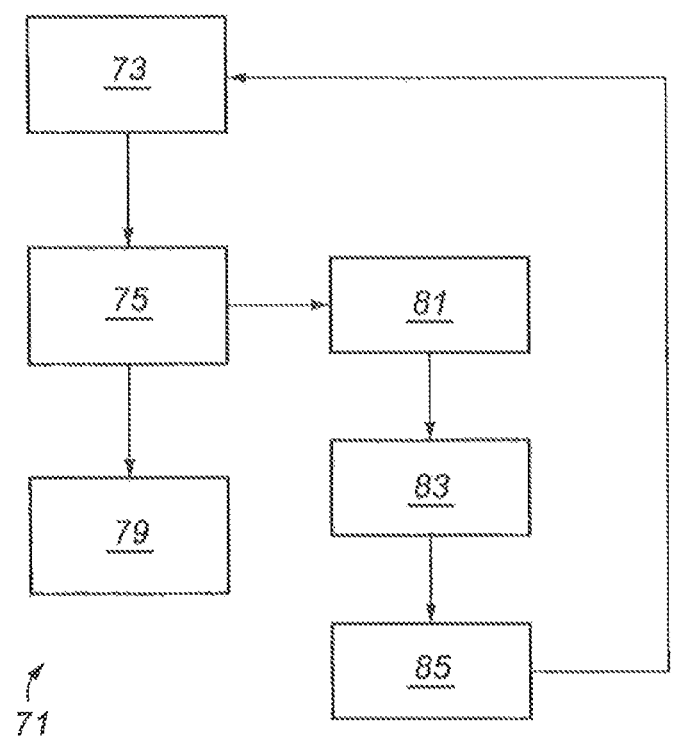
FIG. 7 is a flow diagram showing another embodiment of the method of the invention.

In the embodiment of the present invention shown in FIG. 7, in addition to characterising the state of mineralisation of the tooth, the electrical response of the circuit gives information indicative of the build-up of exogenous proteins and/or lipids in the area of interest. The flow diagram 71 illustrates the transfer of a mineralising agent to the biological material 73. The electrical response of the circuit is then detected 75 and the detected signal is analysed so as to determine whether, and the extent to which, the ultrasonic signal and electrical signal needs to be modified in response to the detected electrical response of the circuit 77. In addition, the detector of the present invention is adapted to detect 81 changes in the electrical response that are as a result of a build up of exogenous proteins, lipids and other materials. Once detected the remineralisation process is interrupted 83 and a conditioning agent is re-applied 85 for a specific period. Thereafter, the process of remineralisation may resume.

The presence of the exogenous proteins and/or lipids may be indicated by the apparatus of the present invention by analysis of the electrical response. In these circumstances, the user will be advised that a re-conditioning step is required and will take the appropriate action to re-apply a conditioning agent.

In another embodiment of the invention, the apparatus is provided with a reference electrode which in this example comprises a small Ag/AgCl wire placed close to the probe electrode. The reference electrode allows more precise control of electrical potential and is of particular use when large currents are required to treat large lesions.

The impedance of the tooth can be measured by the application of an AC signal as described above. Alternatively, a current interruption technique can be used whereby a current is applied for a certain amount of time and then the circuit is broken rapidly using a relay. The decay of the potential with time can give information on the resistance of the tooth.

In addition, the invention can be used in the preconditioning of, for example, a tooth where ultrasonic signals (and generally iontophoresis) are used in preconditioning. A conditioning agent may be propelled into a hypo-mineralised or demineralised caries lesion, by ultrasonic signals (and generally iontophoresis) to optimise the disruption of the exogenous protein and lipid content and then the polarity of the iontophoresis reversed, if required, in order to aid the removal of the proteinacious and other organic material from the hypo-mineralised or demineralised tissue. Examples of suitable agents include bleach, detergent, chaotropic agents such as urea, high phosphate concentrations, cocktails of proteases (e.g. endopeptidases, proteinases and exopeptidases) and any other protein solubilising, disrupting or hydrolysing agent. In this example of the present invention, the probe is attached to a detachable chamber containing a conditioning agent and ultrasound (and optionally iontophoresis) is used with this chamber to propel the conditioning agent into the tooth prior to the remineralising step.

The apparatus and method of the present invention provides electrical feedback during ultrasonic (and generally iontophoretic) conditioning to a detector and a controller which modifies the waveform of the electrical input in response to the detected electrical response of the circuit during conditioning.

According to a third aspect of the present invention a kit comprises apparatus as described above and a mineralising agent. The kit may further comprise a conditioning agent.

The conditioning agent is an oxidising agent, de-proteinising agent or a de-lipidising agent.

According to a fourth aspect of the present invention a mineralising agent comprises a source of phosphate, calcium and hydroxyl/water.

The remineralising agent may comprise casein phosphopeptide-amorphous calcium phosphate (CPP-ACP). The remineralising agent may comprise nano-particles of (calcium) hydroxyapatite.

In a preferred embodiment the remineralising agent contains fluoride. An example of such a remineralising agent is casein phosphopeptide-amorphous calcium fluoride phosphate (CPP-ACFP).

The remineralising agent also advantageously includes one or more remineralisation enhancers. Typically the remineralising enhancers are sources of calcium and phosphate ions.

Examples of remineralisation enhancers include, but are not limited to, Dicalcium phosphate dehydrate (DCPD), mineral brushite; Dicalcium phosphate anhydrous (DCPA), mineral monetite; Octacalcium phosphate (OCP); alpha-tricalcium phosphate (alpha-TCP); beta-tricalcium phosphate (beta-TCP); Amorphous calcium phosphate (ACP); Calcium-deficient hydroxyapatite (CDHA); Hydroxyapatite (HA or OHAp); Fluorapatite (FA or FAp); Tetracalcium phosphate (TTCP or TetCP), mineral hilgenstockite); nano-particles of hydroxyapatite or fluorhydroxyapatite. More preferably, the remineralisation enhancer is strontium.

The remineralising agent may include at least two remineralisation enhancers wherein one of the enhancers is a source of calcium ions and the other is a source of phosphate ions. For example the remineralising agent may include a source of calcium e.g. calcium hydroxide and a source of phosphate e.g. orthophosphoric acid. The ratio of calcium:phosphate in the remineralising agent may be between 1:1 and 22:10. Preferably the ratio of calcium:phosphate is about 10:6 (i.e. 1.67), which represents the ratio of calcium to phosphate ions in calcium hydroxyapatite. Alternatively the ratio of calcium:phosphate in the remineralising agent may be between 9:6 and 22:10. Alternatively still, the ratio of calcium:phosphate in the remineralising agent may be greater than 1:1 but less than 3:2 (i.e. 1.0 up to 1.49).

The remineralising agents may thus be selected from the following:
i) Ca:P ratio=1.67: e.g. Hydroxyapatite (including nano-particles): Fluorapatite.
ii) Ca:P ratio=1.5-2.2 (but not 1.67): e.g. Alpha-Tricalcium phosphate; Beta-Tricalcium phosphate; Amorphous calcium phosphate; Calcium deficient Hydroxyapatite; Tetracalcium phosphate, mineral hilgenstockite.
iii) Ca:P ratio=1-1.49: e.g. Dicalcium phosphate dehydrate, mineral brushite; Dicalcium phosphate anhydrous, mineral monetite.

The remineralising agent may be prepared from its component parts by driving in calcium ions sonophoretically (in aqueous solution) and subsequently driving in phosphate ions (in aqueous solution) with a second sequence of sonophoresis—the calcium and phosphate ions would thus meet within the lesion during the second sequence of sonophoresis and precipitate out as a calcium phosphate mineral (or minerals). The hydroxyl ion of the generated apatite would come from the aqueous solution. The water-soluble calcium-containing agent may be, for example, calcium hydroxide, calcium chloride, or calcium nitrate; the water-soluble phosphate-containing agent may be, for example, orthophosphoric acid ($H_3PO_4$), sodium (or potassium) hydrogen phosphate, sodium (or potassium) dihydrogen phosphate or magnesium phosphate. The calcium agent containing solution may be separate from the phosphate agent containing solution, or combined into one solution.

Thus a preferred method of the invention comprises the steps of: i) pre-conditioning the biological material (hard tissue) to remove protein and/lipids, and ii) applying to the hard tissue a calcium phosphate-containing aqueous solution whilst separately, sequentially or simultaneously applying ultrasound. The pre-conditioning step can be effected with or without the use of ultrasound to drive in the de-proteinisation agent, e.g. sodium hypochlorite. The frequency of this ultrasound can be in the range which will generate cavitation or Ultrasonic streaming.

A further preferred method of the invention comprises the steps of i) pre-conditioning the biological material (hard tissue) to remove protein and/lipids ii) applying to the tissue a calcium-containing aqueous solution or phosphate-containing aqueous solution whilst separately, sequentially or simultaneously applying sonophoresis, and iii) either (a) applying a phosphate-containing aqueous solution where in (ii) a calcium-containing aqueous solution was applied or (b) applying a calcium-containing aqueous solution where in (ii) a phosphate-containing aqueous solution was applied whilst separately, sequentially or simultaneously applying sonophoresis.

The pre-conditioning step is performed, with or without the application of ultrasound, prior to application of the remineralising agent/ultrasound. The pre-conditioning step may further comprise treatment with a hypochlorite and preferably treatment with an acid, more preferably, phosphoric acid.

The method, according to the present invention, may be used for the treatment or alleviation of dental caries and/or dental fluorosis in a mammal. It may also be used for remineralising of hypo-mineralised or de-mineralised (carious) dentine. The present invention also provides a remineralising agent for use in ultrasonic remineralising treatment of hard tissue which has been subject to pre-conditioning to remove protein and/or lipids, the remineralising agent being a source of both phosphate and calcium.

A variety of mineralising agents may be used, including a mixture of mineralising agents. The mineralising agent may depend upon the tissue to be treated. However, preferably, the mineralising agent is a phosphate or calcium source, preferably a source of phosphate and calcium. An especially preferred mineralising agent is casein phosphopeptide-amorphous calcium phosphate (CPP-ACP).

For use in the remineralisation of tooth, the mineralising agent may be a fluoride containing agent as hereinbefore described, such as casein phosphopeptide-amorphous calcium fluoride phosphate (CPP-ACFP). Other mineralising agents may comprise calcium phosphate compounds, such as fluoroapatite, monetite, brushite, amorphous calcium phosphate, hydroxyapatite, etc. Furthermore, it may be possible to incorporate additional elements in the mineralising agent of the invention which may enhance the remineralisation effect, such as strontium. Nano-particles of the mineralising agents, e.g. hydroxyapatite, are a preferred mineralising agent.

It will be understood by the person skilled in the art that the terms hypo-mineralised tissue and demineralised tissue are intended to include any tissue that is deficient in its level of mineralization and includes tissue, such as tooth, that is substantially or completely demineralised, e.g. as a result of the dental caries process, thus including dental caries lesions, or a result of acid erosion, thus including 'surface-softened' enamel or dentine.

The ultrasound may comprise the application of a single frequency or a range of frequencies. Alternatively, the ultrasound may comprise the application of a mixture of frequencies, for example, the combination of frequencies may be applied in specific sequences so as to optimise remineralisation.

Additionally, as previously mentioned, in the method of the present invention a preconditioning step is also included prior to application of the mineralising agent/ultrasound. This preconditioning step is now discussed in more details. The pre-conditioning step may vary but may, for example, comprise the removal of proteins and/or lipids prior to application of the mineralising agent/ultrasound. Although a variety of pre-conditioning steps may be used, preferably, the preconditioning step comprises a variety of processes or a mixture of processes. Any suitable protein removing agent can be used in the preconditioning step of the present invention. The agent is required to reduce the proteinaceous barrier formed over the surface to be treated, such as the pellicle over teeth or the exogenous protein within a caries lesion. The preconditioning step may optionally include the use of ultrasound and the various preconditioning agents, e.g. protein removing agents, may be used in a variety of combinations and/or sequences. Furthermore, any of the pre-conditioning agents may be propelled into a hypomineralised or demineralised region, e.g. caries lesion, by ultrasound to optimise the disruption of the protein layer and removal the proteinacious material from the hypo-mineralised or demineralised tissue. Examples of suitable agents include bleach, detergent, chaotropic agents such as urea, high phosphate concentrations, cocktails of proteases (e.g. endopeptidases, proteinases and exopeptidases) and any other protein solubilising, disrupting or hydrolysing agent. Examples of suitable bleaches include sodium hypochlorite and peroxide bleaches. In a preferred embodiment, the bleach is an alkaline bleach. In a further preferred embodiment the alkaline bleach is sodium hypochlorite. The protein disrupting agent acts to solubilise and partially or wholly remove proteins from the surface of the tooth mineral, e.g. proteins of the pellicle on the tooth surface. However, preferably the preconditioning step comprises treatment with an acid, such as an organic acid, e.g. acetic acid, an inorganic acid, e.g. phosphoric acid, or a bleaching agent, e.g. hypochlorite, for example, sodium hypochlorite. The application of the ultrasound in the lower frequency range acts to generate cavitation during the pre-conditioning step which promotes removal of the exogenous organic material from the surface of and within the lesion.

The mineralising agent may be applied in a variety of forms, for example, in the form of a gel or mousse. For use in the treatment of tooth other oral applications known per se may be used.

Pre-conditioning is preferably carried out not more than one minute before the application of the mineralising agent. More preferably, the mineralising agent is applied almost contemporaneously, i.e. within seconds, of the preconditioning.

A preferred treatment sequence involves repeated conditioning followed by mineralising, particularly in a case where the mineralising agent includes material, such as protein, which is removed in a subsequent conditioning step.

The present invention further provides a method of cosmetic treatment of tissue by application to the tissue of a mineralising agent whilst separately, sequentially or simultaneously applying ultrasound.

It will be further understood by the person skilled in the art that the method of the invention may also be advantageous in the field of orthopaedics, for example, in the treatment of bone pathologies in mammals, i.e. human or animals, such as fractures and/or during surgery.

The present invention provides improved mineralisation of tissue. However, conventional methods of remineralisation of tooth generally comprise remineralisation of the surface tissue, i.e. remineralisation of enamel. It is a particular advantage of the present invention that the method and/or use provide for remineralisation of dentine. Dentine is the term for a hard substance which is related to bone and forms the core of the tooth in mammals and man. Dentine consists to the extent of approximately 30% of a cell-free organic base substance, in particular glycoproteins in which collagen fibres are incorporated. The inorganic constituents are predominantly hydroxyapatite, fluoroapatite and small amounts of carbonates, magnesium and trace elements.

The present invention further provides a kit for use in ultrasonic remineralising treatment of tissue comprising a pre-conditioning agent and a mineralising agent. The remineralising agent may comprise a source of calcium and phosphate ions such as defined herein.

Preferably, the pre-conditioning agent and the remineralising agent are present in the kit in a suitable form for application, for instance, a liquid or a gel form.

The kit may also provide an applicator for applying the, or each, agent to the site of treatment.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Throughout the description and claims of this specification, the words "comprise" and "contain" and variations of the words, for example "comprising" and "comprises", mean "including but not limited to", and are not intended to (and do not) exclude other moieties, additives, components, integers or steps.

Improvements and modifications may be incorporated herein without deviating from the scope of the invention.

What is claimed is:

1. Apparatus for mineralising a biological material, comprising:
   an ultrasonic source, operable to generate an ultrasonic signal,
   an ultrasonic probe and
   at least one mineralising probe, operable to receive a mineralising agent,
   wherein the mineralising agent is transferred from the at least one mineralising probe to the biological material using the ultrasonic signal.

2. Apparatus as claimed in claim 1, further comprising an iontophoresis probe.

3. Apparatus as claimed in claim 1, wherein the ultrasonic probe comprises the at least one mineralising probe.

4. Apparatus as claimed in claim 1, further comprising:
   a first electrode, a second electrode and an electrical signal generator operable to generate an electrical signal between the first and second electrodes,
   a detector, operable to detect an electrical response of the electrical signal between the first and second electrodes, and
   a controller operable to receive the detected electrical response and to control the ultrasonic signal in accordance with the detected electrical response.

5. Apparatus as claimed in claim 4, further comprising:
   a mineralising probe electrode and a modulator, operable to modulate the electrical signal between the mineralising probe electrode and the second electrode and thereby cause the transfer of the mineralising agent to the biological material using the electrical signal.

6. Apparatus as claimed in claim 5, wherein the first electrode comprises the mineralising probe electrode.

7. Apparatus as claimed in claim 5, further comprising a reference electrode operable to control at least one of the modulation of the electrical signal and the ultrasonic signal.

8. Apparatus as claimed in claim 5, wherein the mineralising probe electrode transfers the mineralising agent to the biological material by iontophoresis.

9. Apparatus as claimed in claim 5, operable to apply the modulated electrical signal and to transfer the mineralising agent at least one of separately from, sequentially to and simultaneously with the modulated electrical signal.

10. Apparatus as claimed in claim 4, wherein the controller is operable to control modulation of the electrical signal relative to the detected electrical response.

11. Apparatus as claimed in claim 4, wherein the controller comprises a first software module having a dataset which describes a characteristic electrical response of a sample biological material at a plurality of stages of mineralisation, and a second software module which compares the dataset with the detected electrical response and determines at least one required modification of at least one of the electrical signal and the ultrasonic signal.

12. Apparatus as claimed in claim 11, wherein the second software module applies a function which defines a relationship between the mineralisation and the electrical response in order to compare the dataset with the detected electrical response and to thereby determine a required modification of at least one of the electrical signal and the ultrasonic signal.

13. Apparatus as claimed in claim 11, wherein the second software module applies a look-up table containing information on at least one of the electrical response and the mineralisation of the biological material, to compare the dataset with the detected electrical response and to determine at least one required modification of at least one of the electrical signal and the ultrasonic signal.

14. Apparatus as claimed in claim 4, wherein the detector is operable to determine, from the electrical response, presence of at least one of exogenous proteins and lipids on or in the biological material.

15. Apparatus as claimed in claim 4, operable to apply the ultrasonic signal and the electrical signal at least one of separately from, sequentially to and simultaneously with one another.

16. Apparatus as claimed in claim 1, further comprising means for applying a conditioning agent.

17. Apparatus as claimed in claim 16, wherein the conditioning agent comprises at least one of an oxidising agent, a de-proteinising agent and a de-lipidising agent.

18. Apparatus as claimed in claim 1, operable to apply the ultrasonic signal and to transfer the mineralising agent at least one of separately from, sequentially to and simultaneously with the ultrasonic signal.

19. Apparatus as claimed in claim 1, adapted for use with hard tissue biological material.

20. Apparatus as claimed in claim 19, wherein the hard tissue biological material comprises at least one of teeth or bones.

21. A kit comprising:
(i) apparatus for mineralising a biological material, comprising
an ultrasonic source, operable to generate an ultrasonic signal,
an ultrasonic probe and
at least one mineralising probe, and
(ii) a mineralisation agent for mineralising biological material,
wherein the at least one mineralising probe is operable to receive the mineralising agent and to transfer the mineralising agent from the at least one mineralising probe to the biological material using the ultrasonic signal.

22. A kit as claimed in claim 21, further comprising a conditioning agent.

* * * * *